United States Patent
Dyer et al.

(10) Patent No.: US 9,057,064 B1
(45) Date of Patent: Jun. 16, 2015

(54) METHOD AND APPARATUS FOR EXTRACTING DNA FROM A BIOLOGICAL SAMPLE

(75) Inventors: Rex Bryan Dyer, East Peoria, IL (US); Beth Susan Turnbull-Dyer, East Peoria, IL (US); Kenneth L. Owen, Peoria, IL (US); John G. Schierer, Marquette Heights, IL (US)

(73) Assignee: AG-DEFENSE SYSTEMS, INC., Peoria, IL (US)

( * ) Notice: Subject to any disclaimer, the term of this patent is extended or adjusted under 35 U.S.C. 154(b) by 1032 days.

(21) Appl. No.: 13/149,299

(22) Filed: May 31, 2011

Related U.S. Application Data

(63) Continuation-in-part of application No. 12/392,683, filed on Feb. 25, 2009, now abandoned.

(51) Int. Cl.
| | |
|---|---|
| *C12N 1/06* | (2006.01) |
| *C12M 3/08* | (2006.01) |
| *C12N 15/10* | (2006.01) |
| *C12M 1/00* | (2006.01) |
| *C12M 1/33* | (2006.01) |

(52) U.S. Cl.
CPC ........... *C12N 15/1003* (2013.01); *C12M 45/09* (2013.01); *C12M 45/02* (2013.01); *C12M 47/06* (2013.01)

(58) Field of Classification Search
CPC ......... B01L 7/52; B01L 3/5027; B01L 3/502; C12Q 1/689; C12N 15/1003; C12N 1/06; C12M 45/02; C12M 45/09; C12M 47/06
USPC ............................................ 435/286.6, 287.2
See application file for complete search history.

(56) References Cited

U.S. PATENT DOCUMENTS

| | | | |
|---|---|---|---|
| 6,589,785 B1 * | 7/2003 | Mullner et al. ................ | 435/325 |
| 2002/0197631 A1 * | 12/2002 | Lawrence et al. ................. | 435/6 |

* cited by examiner

*Primary Examiner* — Michael Hobbs
(74) *Attorney, Agent, or Firm* — Husch Blackwell LLP

(57) ABSTRACT

A method of extracting DNA from a biological sample includes the steps of freezing a biological sample; mechanically breaking down the sample to produce a processed sample; mixing the processed sample with a lysis solution; and cycling the mixture through a series of pressure fluctuations to produce a resulting lysate. The method may further include the steps of exposing the lysate to a material that binds to DNA present in the sample and collecting the DNA from the sample using an elution solution. An apparatus for practicing the method includes a first segment for mechanically breaking down the sample; a second segment for pressurizing a mixture of the processed sample and lysis solution to produce a lysate; and wherein the first segment is fluidly coupled to the second segment. The apparatus may also include a third segment in which the lysate is exposed to the binding material.

7 Claims, 13 Drawing Sheets

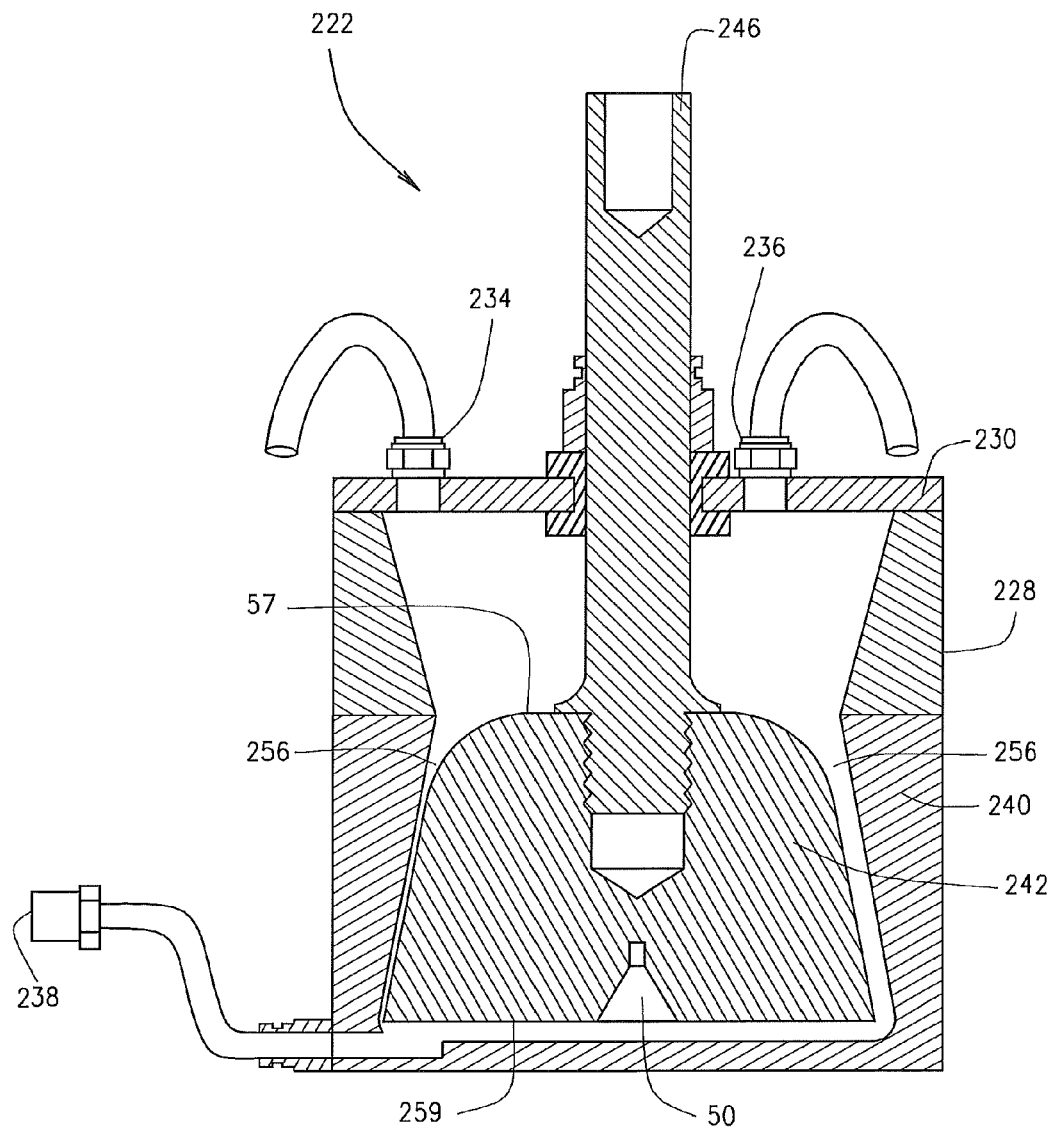
F I G . 1 0 A

METHOD AND APPARATUS FOR EXTRACTING DNA FROM A BIOLOGICAL SAMPLE

CROSS-REFERENCE TO RELATED APPLICATION

This application is a continuation-in-part application of prior non-provisional patent application Ser. No. 12/392,683 entitled Portable Microorganism Detection Unit, filed on Feb. 25, 2009. The disclosure of application Ser. No. 12/392,683 is incorporated herein by reference in its entirety.

BACKGROUND OF THE INVENTION

The present invention relates in general to methods and apparatus for rapidly and efficiently extracting nucleic acid from a biological sample and, in one embodiment, to a portable device for extracting nucleic acid, such as DNA or RNA, from a food sample in order to detect pathogens on food and crops. In addition to food microorganism detection, the present invention can be applied to detection of microorganisms in the medical and veterinary industries, surveillance of microorganisms in environmental applications, applications in homeland security and military field operations and routine microorganism screening in the pharmaceutical industry.

The need to detect microorganisms in food products has increased in recent years. Specifically, food products may be contaminated with pathogens either intentionally or unintentionally. Unintentional adulteration of crops pertains to environmental pathogens normally present and that contaminate the food product during normal food processing and handling procedures. Intentional adulteration of pathogens refers to a deliberate planting of pathogens on food or crops as would occur in an act of bioterrorism.

Often food products are tested for such microorganisms at the time that the food product is made. More often, the existence of such microorganisms does not become evident until after the food products have been sold at retail stores. Detecting a microorganism at such a late time generally results in a recall of vast amounts of food and/or a need to dispose of entire crops and whole food sources. Such recalls put an economic burden on food related businesses and pose a public health problem.

Most food manufacturers regularly analyze their food products. However, the detection systems in use today generally require the crop and/or food product to be tested at a laboratory facility that is remote from the processing plant or the field. Accordingly, the testing is time consuming and costly. Moreover, during the time of testing, contaminated food products may make their way into general commerce only to be recalled at a later date and after consumption.

Most conventional, manual methods of extracting nucleic acid are executed within a normal lab facility comprised of multiple steps. If the material to be processed is a solid matrix such as a food or tissue sample, the first step is to grind or otherwise mince the material. The process of grinding or mincing increases the surface area allowing the cell walls of microorganism embedded in the matrix to be exposed to the second step of cell lysis. The cell may be lysed by chemical treatment, boiling, enzymatic digestion of the cell wall, or by mechanical forces. Lysis releases the nucleic acid (i.e. DNA or RNA) from the cell and makes it available for manipulation. Following lysis, filtration may be employed to remove debris from the ground material. Subsequent organic extraction with solvents such as phenol and chloroform followed by centrifugation serves to separate proteins and lipids. In a third step, the DNA may be further purified via precipitation with salt and alcohol which also involves a centrifugation to pellet the DNA and allow removal of the supernatant. The DNA pellet may then be washed in an alcohol solution prior to resuspension in a tris-based buffer for analysis. DNA precipitation and washing serves to remove potential inhibitors that may affect downstream analytical approaches such as polymerase chain reaction (PCR). In addition to or in place of precipitation, the DNA may be purified over a column containing a solid phase material. After the DNA binds to the column, impurities can be removed by washing the column. The purified DNA can then be eluted off the column in a low salt aqueous solution for subsequent downstream analysis.

U.S. Pat. Nos. 6,120,985, 6,111,096, and 6,274,726, each issued to Laugharn, Jr. et al. describe methods for cell lysis of biological materials for purifying DNA for downstream applications. The methods include exposing biological cells to elevated pressures in a pressure chamber. In one patent the cells are cooled to subzero temperatures prior to placing them in the chamber. The sample chamber includes a filter and a solid phase material. The filter operates to remove cell debris from the sample. The solid phase material includes any one of silica gel, glass, plastic, membrane, resins, hydroxyapatite or tethered specific binding molecules or metals that are used to bind to nucleic acids in the sample. After the nucleic acids in the sample bind to the solid phase, the pressure in the chamber is increased to release the nucleic acids from the solid phase. The cartridge or chip with the solid phase material also contains electrodes to move biomolecules towards the solid phase for binding or towards a waste or collection reservoir. Modulating the pressure at the solid phase changes the binding of the biomolecule on the solid phase material. However, known devices for isolating and purifying DNA do not allow for integrated point-of-use analysis with solid food/tissue matrices.

The inventors of the present invention previously conceived combined mincing and cell lysis in one process prior to the purification step by putting a whole food/tissue sample in the lysis solution and then putting the solution in the grinding/mincing chamber of a lysis tube for food/tissue comminution. The tube includes an upper sample preparation chamber having at least one mincing disk to mince the sample, a filter to filter particulate matter from the extract, and a third chamber having a binding material configured to bind to the DNA of the extract. The whole food/tissue sample is forced through pores of lysis disks to mince the food/tissue sample and then, the minced food/tissue sample is filtered prior to the purification step.

The present invention aims to provide an alternative system and method for extracting nucleic acid from a nucleic acid-containing sample.

SUMMARY OF THE INVENTION

Accordingly, it is desirable to provide a portable microorganism detection device that is capable of detecting microorganisms on food items, crops, seeds, or other biological matter in a point-of-use manner. Specifically, it is desirable to have a device that can be operated at a location that may be remote from laboratory facilities to provide immediate analysis. It is also desirable to have a device that is capable of analyzing seeds prior to crop planting. As will be appreciated by one of ordinary skill in the art, the present invention may be used to detect microorganisms on a vast array of products or environmental samples.

In one aspect, the present invention includes a portable device for detecting a microorganism in a biological sample.

The device includes a DNA extraction tube, a chip, and a portable control unit. The DNA extraction tube is configured to give a purified DNA eluate after extracting DNA from the sample. The tube includes an upper chamber having at least one mincing disk to mince the sample, a filter to filter particulate matter from the extract, and a lower chamber having a binding material configured to bind to the DNA of the extract. The chip is configured to retain the eluate for analysis. The chip includes reaction chambers disposed for an isothermal polymerase chain reaction to amplify the DNA in the eluate for detection. The portable control unit is configured to receive the chip and analyze the amplified DNA on the chip. In one embodiment, the device is configured to detect, for example, bioterrorism molecules and/or plant and food pathogens.

In another aspect, the present invention includes a DNA extraction tube for extracting DNA from a biological sample. The tube includes an upper chamber and a lower chamber. The upper chamber is configured to receive the sample, and includes at least one mincing disk to mince the sample. The mincing disk is configured with serrated edges to facilitate mincing the sample. The lower chamber is configured to receive an extract from the upper chamber after a valve opens to let the extract pass through a filter for removing particulate matter. The lower chamber includes a binding material configured to bind to DNA from the extract. The lower chamber further includes an inlet for channeling fluids to the lower chamber and an outlet for channeling fluids from the lower chamber. In another embodiment, the extraction tube may have a plurality of inlets and outlets for channeling fluid into and out of the lower chamber. In one embodiment, the extraction tube includes a plurality of consecutive mincing disks having incrementally smaller pore sizes.

In yet another aspect, the present invention includes a chip for analyzing DNA in a biological sample. The chip includes reaction chambers disposed for a polymerase chain reaction, including but not limited to isothermal methods, to amplify the DNA for detection. The chip is also sized for insertion into a portable control unit that analyzes the DNA after amplification. In the exemplary embodiment, the chip further includes reagents in the reaction chambers for amplification of the DNA. The reagents include of lyophilized nucleotides, DNA polymerase, pathogen specific primers, buffers and salts, and/or fluorescent labeling molecules. The DNA is analyzed to detect, for example, food and plant pathogens and/or bioterrorism molecules.

In accordance with another aspect of the invention, it would be desirable to provide a portable device for extracting nucleic acid, such as DNA or RNA, from a food, crop, tissue or other biological sample to be used with a microorganism detection device that is capable of detecting microorganisms in a point-of-use manner. As will be appreciated by one of ordinary skill in the art, the present invention may be used in additional applications to detect microorganisms on a vast array of products and environmental samples.

There is also provided a method for isolating nucleic acid that comprises: (a) quick freezing a biological sample with a suitable unit; (b) mechanically processing the frozen biological sample in a first chamber; (c) applying a lysis solution to the processed sample; (d) cycling the processed sample solution through a series of pressure fluctuations, resulting in cell lysis; (e) binding or capturing the DNA from the lysate on a column by cycling the lysate through the column; (f) washing the column bound DNA to remove other cellular molecules and PCR inhibitors by cycling wash solutions through the column; and (g) eluting nucleic acid from the column for subsequent analysis by cycling elution solution through the column.

In one aspect, the present invention includes a portable device for detecting microorganism in a biological sample. The device includes a DNA extraction device, a chip, and a portable control unit. The DNA extraction device is configured to give a purified DNA eluate after extracting and purifying DNA from the sample. The DNA extraction device includes a first chamber or portion for grinding, mincing, pulverizing, or otherwise mechanically processing a biological sample, a second chamber or portion for pressurizing the processed sample, and a third chamber or portion having a binding material configured to bind to the DNA of the extract. The chip is configured to retain the eluate for analysis. The chip includes reaction chambers disposed for a polymerase chain reaction (including isothermal methods) to amplify the DNA in the eluate for detection. The portable control unit is configured to receive the chip and analyze the amplified DNA on the chip. In one embodiment, the device is configured to detect, for example, bioterrorism molecules and/or plant and food pathogens. Those of ordinary skill in the art will recognize that this device may be applied in a wide variety of industries and applications.

In another aspect, there is provided a first chamber or portion for mechanically processing a biological sample under the influence of a centrifugally responsive inner grinding member acting against an outer grinding member. The first chamber or portion for grinding the sample includes a cylindrical body, a top cover, one or more inlet openings, an outlet, an outer grinding member and an inner grinding member positioned within the outer grinding member. The top cover is disposed at the top of the cylindrical body and secured to the cylindrical body by multiple securing means. The first chamber is connected to a pressure source by a valve. The top cover may also include an inlet opening selectively connected to a liquid nitrogen source to freeze the sample, a lysis solution source, and sources for addition of cleaning agents after a sample has been processed. The control unit is capable of controlling movement and pressure within the grinding/mincing chamber. The crushing or grinding chamber of the DNA extraction device includes a motor for rotating the inner grinding member. The inner grinding member is positioned offset from the center of the grinding chamber and oscillates in an asymmetric fashion. The inner grinding member is supported by a drive shaft during operation of the inner grinding member. The biological sample is ground as it is banged and squeezed against the inner surface of the outer grind member from the outer surface of the inner grinding member oscillating in an asymmetric manner.

In yet another aspect, the present invention includes a second chamber or portion for pressurizing the mixture of the processed biological sample and the lysis solution. The second segment includes two pairs of ports and two circulating pipes or tubes which connect the corresponding ports for allowing the biological sample to enter or to exit from the second segment for passage and compression through an orifice or stricture. The second segment is connected to a source of pressurized air but may also be pressurized by other means familiar to those skilled in the art. Movement of the liquid out of the orifice or stricture results in a drop in pressure on the liquid. Pressure of liquid drops faster than the intracellular pressure, resulting in cell explosion. Note that cell lysis can occur through the introduction of shear forces to the liquid as well. Cell explosion or lysis releases intracellular contents such as fats, proteins, carbohydrates, RNA and DNA. Pressurization occurs during each passage of the processed biological sample through the stricture or orifice disposed within the second segment. As high pressure is applied to the second segment, pressurization occurs during multiple passages of the liquid through the orifice. The mixture of the processed biological sample and the lysis solution is passed multiple times through a compressing stricture or orifice to cycle between pressure increases and decreases.

The third chamber includes a binding material configured to bind to DNA from the extract. The third chamber further includes one or more inlets for channeling fluids to the third chamber and one or more outlets for channeling fluids from the third chamber. The third chamber may be designed to be disposable or reusable.

In yet another aspect, the present invention includes a chip for analyzing DNA in a biological sample. The chip includes reaction chambers disposed for a polymerase chain reaction (including isothermal methods) to amplify the targeted DNA for detection. The chip is also sized for insertion into a portable control unit that analyzes the DNA during amplification. In the exemplary embodiment, the chip further includes one or more reagents in the reaction chambers for amplification of the targeted DNA. Possible reagents include, for example, lyophilized nucleotides, DNA polymerase, pathogen specific primers, buffers and salts, and/or fluorescent labeling molecules. The DNA is analyzed to detect, for example, food and plant pathogens, bioterrorism molecules, or medical and veterinary pathogens.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 10A is a cross-sectional view of the grinding chamber shown in FIG. 10.

It should be understood that the present drawings are not necessarily to scale. In certain instances, details which are not necessary for an understanding of the present invention or which render other details difficult to perceive may have been omitted. It should also be understood that the present invention is not necessarily limited to the particular embodiments illustrated herein. Like numbers utilized throughout the various figures designate like or similar parts or structure.

DETAILED DESCRIPTION OF THE PREFERRED EMBODIMENTS

The following description of the preferred embodiment(s) is merely exemplary in nature and is in no way intended to limit the invention, its application, or uses. The present invention, as shown in FIGS. 1-7 is a portable device 10 for detecting microorganisms in a biological sample. Specifically, in the exemplary embodiment, the device 10 is configured to detect, for example, plant and food pathogens and bioterrorism molecules in seeds, crops, and other food products. For example, the device 10 may be configured to detect pathogens such as soybean rust, wheat scab, corn ear rot, *Salmonella, Listeria, Escherichia coli*, and/or bioterrorism threats such as anthrax, bubonic plague, and/or yellow fever that are contained in biological samples such as meat, bottled water, fresh vegetables, dairy, seafood, and grains. The device 10 is portable so that the detection can take place at a point-of-use or, for example, at the location where the food is grown and/or produced. Accordingly, the biological sample is not required to be taken to a laboratory facility to be analyzed.

Figure 1:
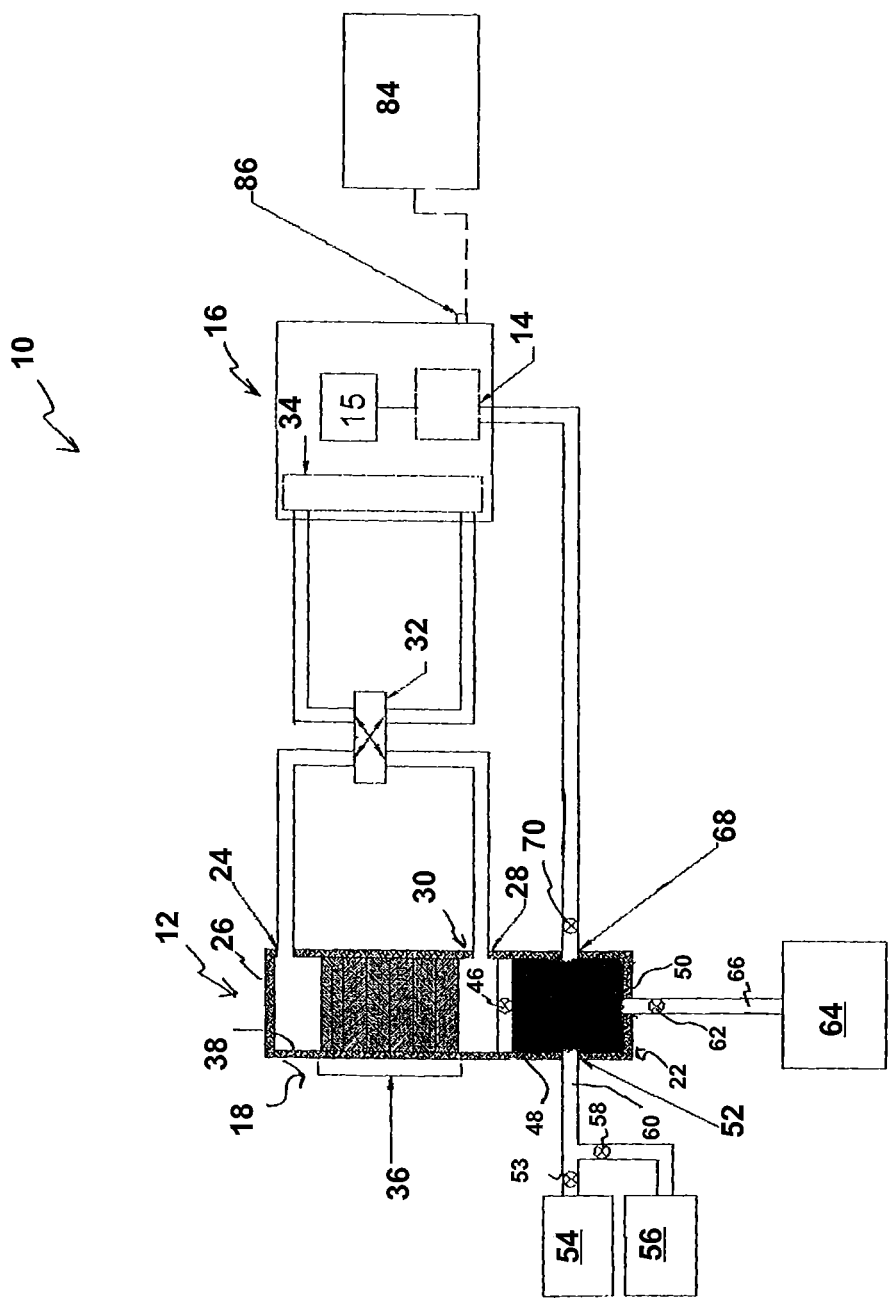
FIG. 1 is a schematic view of a system for detecting microorganisms in a biological sample.

As shown in FIG. 1, the device 10 includes a DNA extraction tube 12 for extracting and purifying a DNA eluate from the sample, a chip 14 configured to retain and react with the eluate to specifically amplify a portion of the DNA, and a portable control unit 16 configured to pressurize the DNA extraction tube 12. The control unit 16 is also configured to receive the chip 14 and analyze the amplified DNA. Although the present invention is described with respect to detecting microorganisms on food products, as will be appreciated by one of ordinary skill in the art, the present invention may be used to detect microorganisms on a vast array of products.

Figure 2:
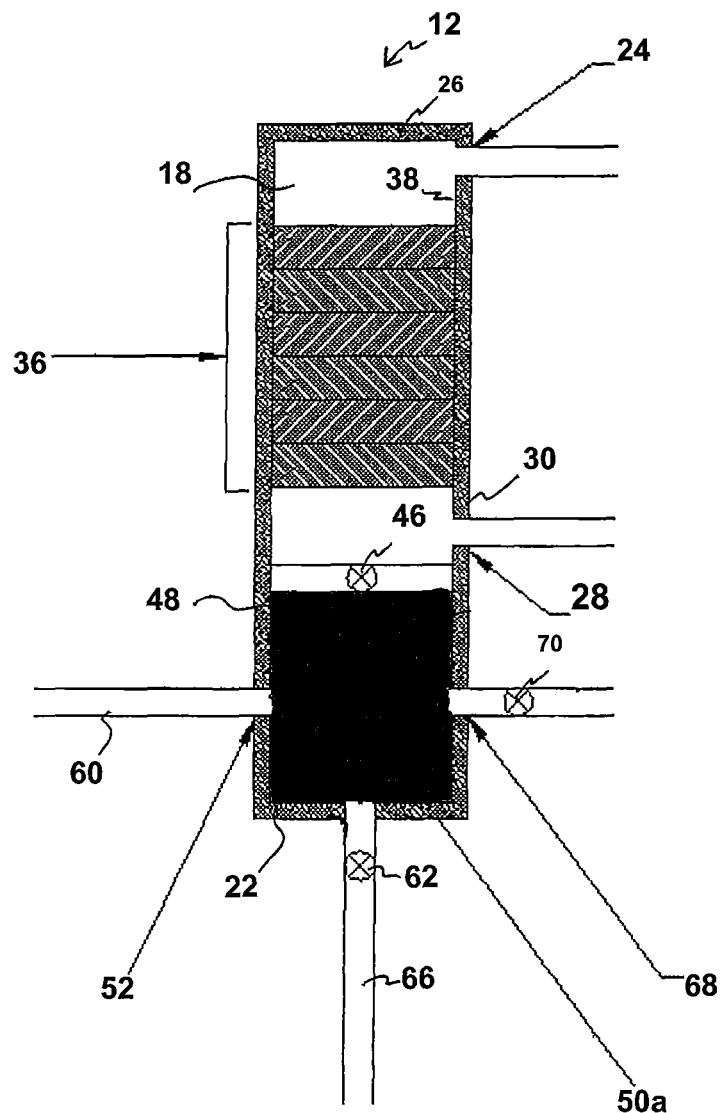
FIG. 2 is a schematic view of a DNA extraction tube used with the system shown in FIG. 1.

The DNA extraction tube 12, as shown in FIG. 2, includes two chambers separated by a filter. Specifically, an upper chamber 18, and a lower chamber 22. The sample is placed in the upper chamber of the extraction tube 12 with a liquid extraction buffer. In the exemplary embodiment, the sample is approximately 25 grams. The solution is then subject to varying pressures to extract the DNA. Specifically, the upper chamber 18 includes a pair of high pressure ports. A first high pressure port 24 is disposed at an upper end 26 of the upper chamber 18, and a second high pressure port 28 is disposed at a lower end 30 of the upper chamber 18. The high pressure ports are fluidly coupled to a two-way solenoid valve 32, which is coupled to a pressure module 34 in the control unit 16. The control unit 16 controls the pressure within the upper chamber 18 by alternating high pressure between the two high pressure ports 24, 28. More specifically, the solenoid valve 32 alternates the high pressure between the first high pressure port 24 and the second high pressure port 28, thereby causing the sample to move in alternating directions through the upper chamber 18. For example, when the high pressure is applied to the first high pressure port 24, the sample is forced downward through the upper chamber 18. Alternatively, when the high pressure is applied to the second high pressure port 28, the sample is forced upward through the upper chamber 18. The applied pressure at each end of the upper chamber 18 may be used to move a piston that compresses and moves the fluid and the sample through the lysis disk. Pressure relief mechanisms may be incorporated to facilitate fluid flow.

Figure 3:
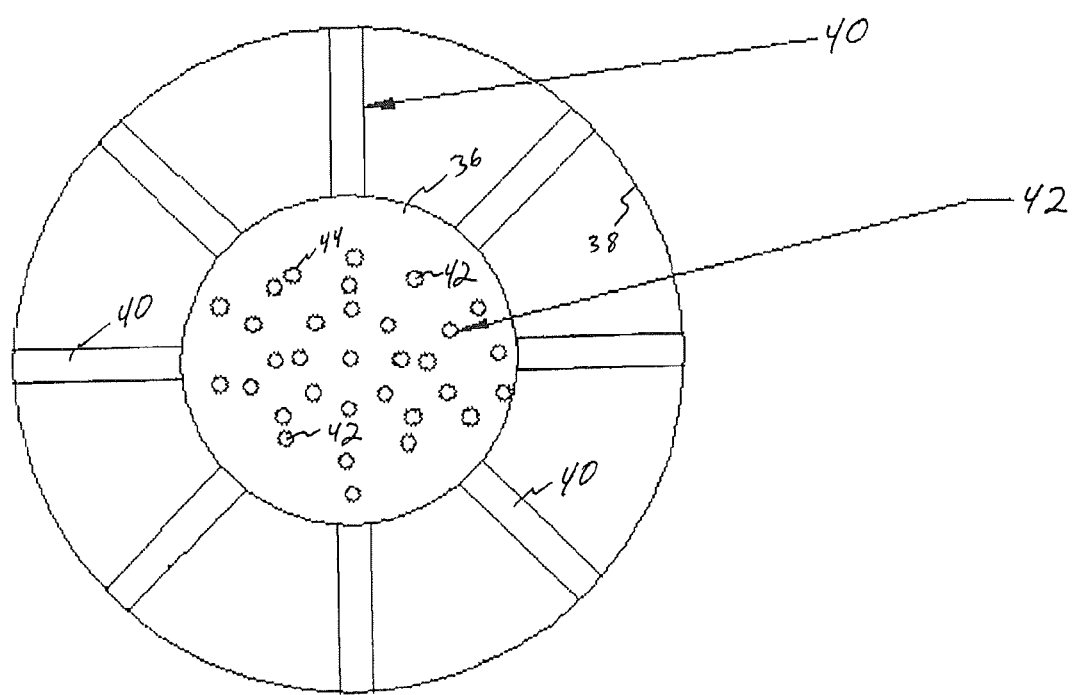
FIG. 3 is a top view of a lysis disc used with the DNA extraction tube shown in FIG. 2.
Figure 4:
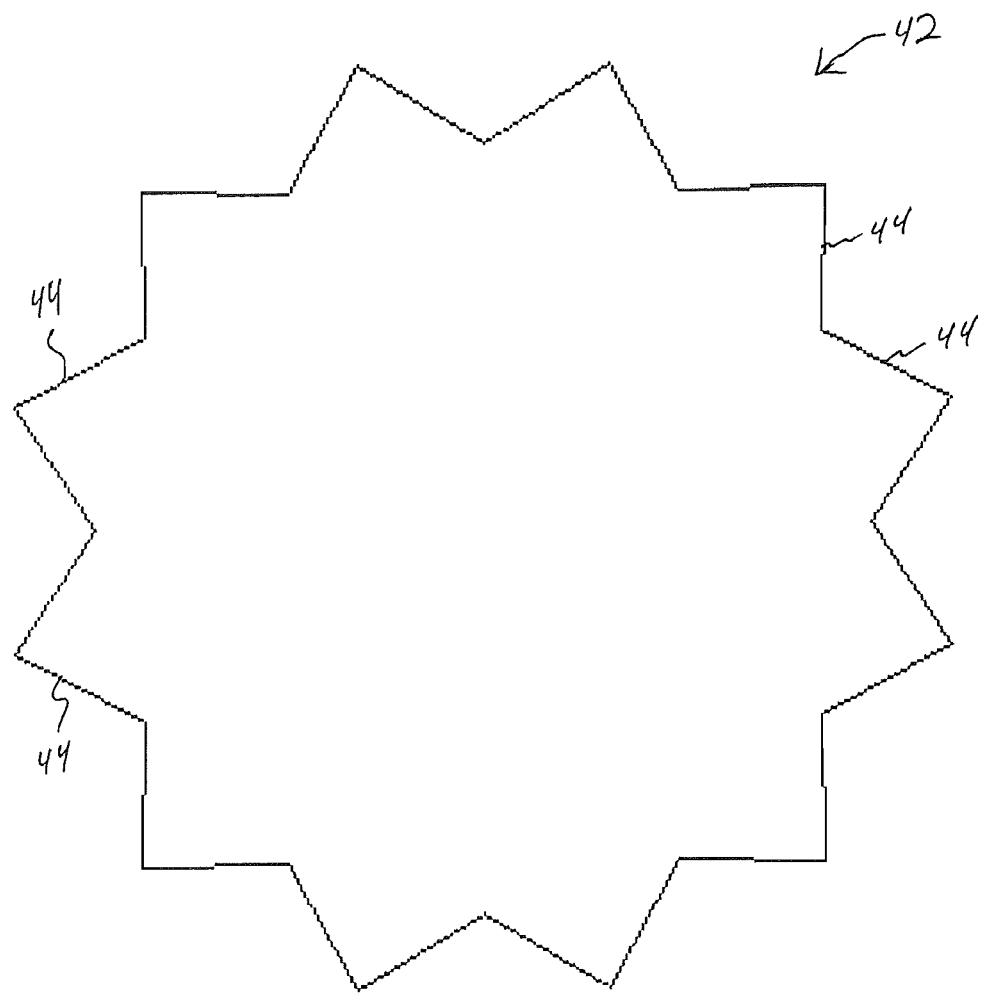
FIG. 4 is a top view of a pore defined in the lysis disc shown in FIG. 3.

The upper chamber 18 includes at least one mincing disk 36, as shown in FIG. 3, positioned between the first high pressure port 24 and the second high pressure port 28. The mincing disk 36 is secured to the inner surfaces 38 of the DNA extraction tube 12 via a locking element 40 that secures the mincing disk 36 during the application of high pressure to the upper chamber 18. The mincing disk 36 further includes a plurality of pores 42 extending through the disk 36. As high pressure is applied to the upper chamber 18 in alternating directions, the sample is forced upward and downward through the mincing disk 36 to mince the sample so that the sample material ruptures, leading to the extraction of biomolecules into the extraction buffer, resulting in the formation of a lysed solution. In the exemplary embodiment, the pores 42 and/or the locking element 40 include serrated edges 44 configured to further mince the sample as it moves through the mincing disk 36. FIG. 4 illustrates one example of the serrated edges 44 of the pores 42. As will be appreciated by one of ordinary skill in the art, the serrated edges 44 are not limited to those shown in FIG. 4, but rather, the serrated edges 44 may include various geometrical forms. Moreover, in one embodiment, as shown in FIG. 1, the upper chamber 18 includes a plurality of mincing disks 36 configured with incrementally smaller pore sizes so that the sample is minced into successively smaller pieces as it is forced through the disks 36.

In one embodiment, a premincing step is included that utilizes a stator/rotor positioned in the upper chamber 18. The rotating blade draws fluid and the sample into the stator and chops the sample. The chopped sample is forced out of holes in the stator to aid in further mincing. This premincing step occurs prior to forcing the sample through the mincing disks 36 via pressure. In addition, in one embodiment, the pressure in the system is combined with methods such as ultrasonics. In a further embodiment, a hypotonic solution is used to separate the sample by flowing water into the cells of the sample causing them to swell and burst. In another embodiment, cycles of freeze/thawing leads to repetitive ice crystal formation which helps to break open the cell membranes of the sample.

The DNA extraction tube 12 includes a valve 46 positioned between the upper chamber 18 and the lower chamber 22 to seal the upper chamber 18 from the lower chamber 22. Accordingly, as high pressure is being applied to the upper chamber 18, the valve 46 is closed to retain the lysed solution within the upper chamber 18. After the solution is thoroughly minced, the valve 46 is opened to allow the lysed solution to flow through a filter 48 that is configured to filter particulate matter from the lysed solution formed in the upper chamber 18. After flowing through the filter 48, the filtered solution flows into the lower chamber 22 of the DNA extraction tube.

The lower chamber 22 includes a binding material 50 that binds to the DNA of the filtered solution. In the exemplary embodiment, the binding material 50 includes silica beads 50a that bind to the DNA in the filtered solution. In addition to silica beads, other DNA binding reagents may be employed including silica gel, silica membrane, glass fiber, diatomaceous earth, ion-exchange resin, iron oxide particles or ligand exchange resins. DNA molecules bind to silica, glass, and diatomaceous earth in the presence of high salt concentrations (e.g. Sodium Iodide or Guanidinium Hydrochloride) and low pH. After washing in an ethanol containing high salt buffer, the DNA can be eluted from the silica, glass or diatomaceous earth in a high pH (e.g. pH=8 to 8.5) buffer with low salt concentrations. Ion exchange resins and iron-oxide take advantage of charge-charge interactions for binding DNA. For example, diethylaminoethanol (DEAE) has a positive charge under low salt and low pH conditions and will bind to the negative charge on the DNA phosphate backbone. DNA can be eluted from DEAE under high salt and high pH conditions. The resin or support for ion exchangers can consist of silica, cellulose, dextran or agarose. Iron oxide has the added advantage of magnetism to facilitate collection and concentration of the DNA bound iron-oxide particles.

The lower chamber 22 also includes an inlet 52 for channeling fluids into the lower chamber 22. The inlet 52 is fluidly coupled to an elution tank 54 and a wash buffer tank 56. A valve 58 is positioned within a port 60 coupled to each tank to allow selective flow of either a wash buffer or a hot elution buffer into the lower chamber 22. After the DNA has bound to the binding material 50, a wash solution is channeled through the inlet 52 into the lower chamber 22 to wash the binding material. A waste valve 62 is then opened to channel waste from the lower chamber 22 to a waste chamber 64 that is fluidly coupled to the lower chamber 22 via a waste port 66. The elution buffer is then channeled into the lower chamber 22 to form an eluate in the lower chamber 22. The eluate is channeled from the DNA extraction tube 12 through an elution outlet 68 via an elution valve 70.

More specifically, during extraction of the DNA, the DNA in the filtered solution binds to the silica beads 50a forming a bead slurry. The bead slurry is then mixed by fluid flow or vibration for an incubation period of approximately five minutes, After the incubation period, the solution is drained through the waste port 66 leaving the silica beads 50a having DNA bound thereto. The beads 50a are then washed with the wash solution. For example, the beads 50a may undergo two washes for approximately five minutes each. The wash solution is then drained off and the hot elution buffer having a temperature of approximately 60 degrees Celsius is added to the lower chamber and mixed with the silica beads 50a for approximately five minutes to form the eluate. The eluate is drained through the elution outlet 68 to the chip 14. In the exemplary embodiment, at least one of circuitry, micropumps, microvalves, and/or microheaters/coolers are used to move the eluate from the extraction tube 12 to the chip 14 and/or to maintain a uniform temperature of the eluate when moving the eluate.

Figure 5:
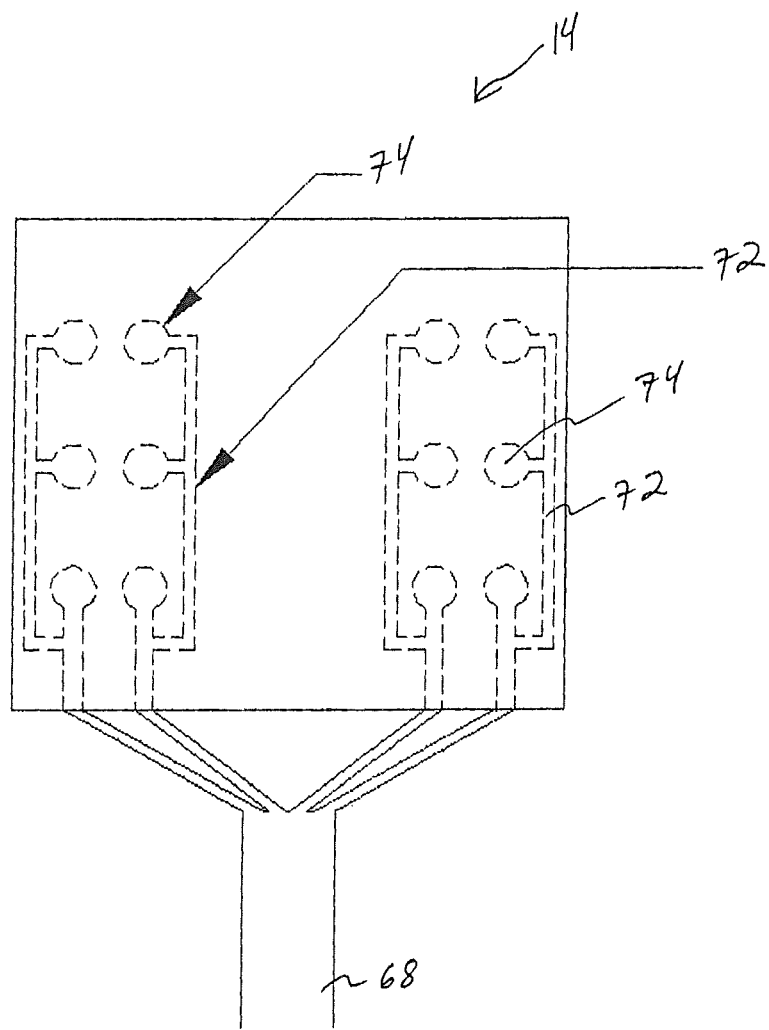
FIG. 5 is a schematic view of a chip used with the system shown in FIG. 1.

As shown in FIG. 5, the chip 14 includes a plurality of microchannels 72 in fluid communication with a plurality of reaction chambers 74 etched within the chip 14. The eluate is channeled via the microchannels 72 to the reaction chambers 74 where a polymerase chain reaction takes place (PCR) to amplify the DNA in the eluate for detection. Specifically, the reaction chambers 74 include reagents, for example lyophilized nucleotides, DNA polymerase, pathogen specific primers, fluorescent labeling molecules such as SYBR green, and/or reagents specific to a type of PCR that are disposed to create a PCR reaction that specifically amplifies a portion of the DNA on the chip 14. It will be appreciated by one of ordinary skill in the art that the number, size, and orientation of the microchannels 72 and reaction chambers 74 may vary depending on the application of the chip 14. Specifically, the chip 14 is configured to be customized for the detection of various microorganisms. The number, size, and orientation of the microchannels 72 and the reaction chambers 74 may vary based on the particular microorganism sought to be detected. Moreover, in one embodiment, the chip 14 may be configured to detect multiple microorganisms through a single analysis. For example, the meat processing industry is concerned mainly with *Escherichia coli, Listeria monocytogenes* and *Salmonella* species. Customized cards for detecting these pathogens could be developed. Processors of fresh fruits and vegetables focus on bacteria such as *E. coli, Salmonella, Vibrio cholera*, and *Shigella*; protozoa such as *Cryptosporidium parvum, Toxoplasma gondii, Giardia lamblia, Cyclospora cayetanensis*; and viruses such as Norwalk and Hepatitis A. For this food processor, custom bacterial, protozoan and viral cards or various combinations could be developed. The dairy industry is concerned with bacterial species from the following genera: *Psuedomonas, Bacillus, Clostridium, Corynebacterium, Arthrobacter, Lactobacillus, Microbacterium, Micrococcus, Streptococcus, Listeria, Escherichia, Yersenia, Salmonella*, and *Campylobacter*.

Figure 6:
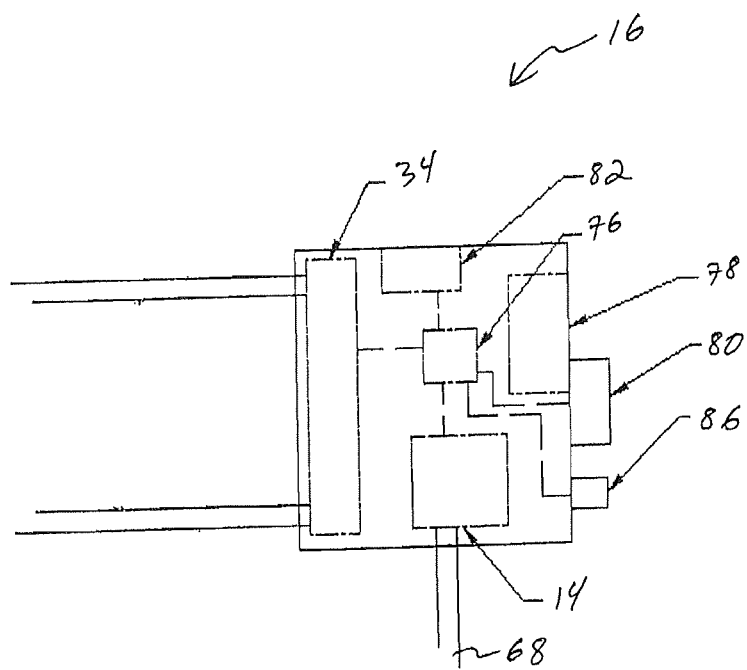
FIG. 6 is a schematic view of a portable control unit used with the system shown in FIG. 1.
Figure 7:
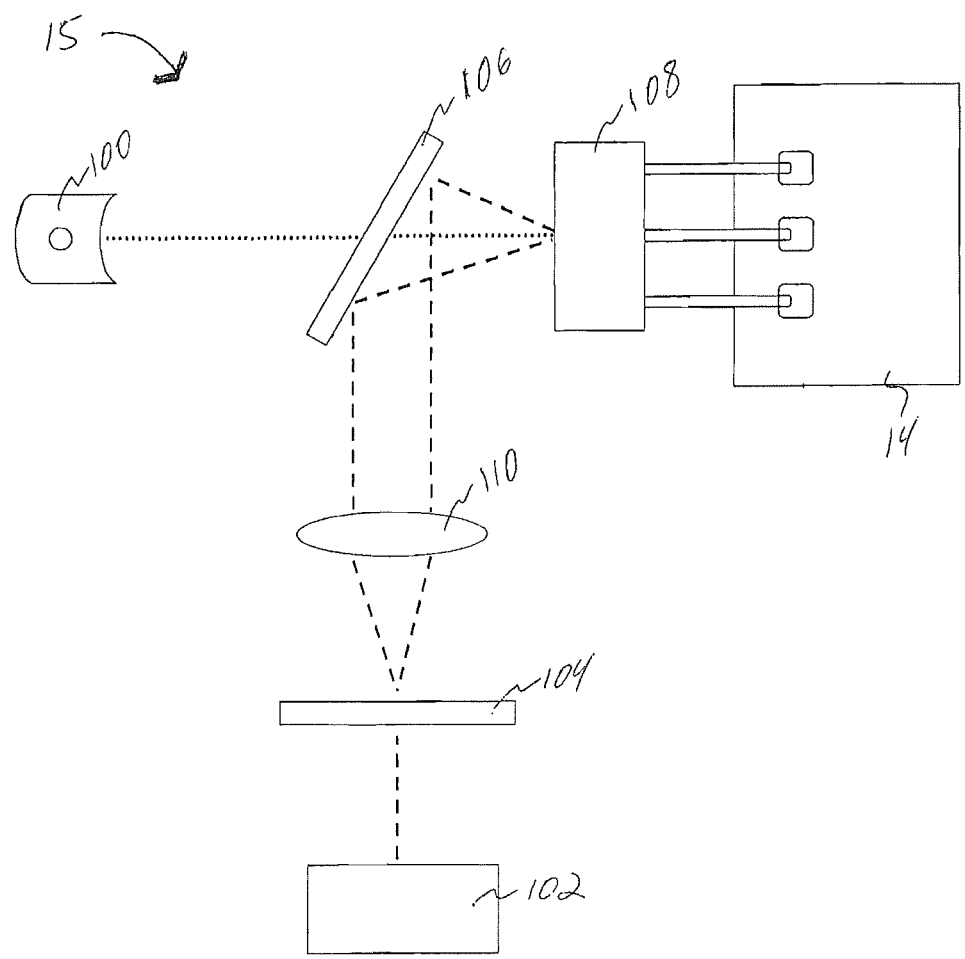
FIG. 7 is a schematic view of the fluorescent detection system used with the system shown in FIG. 1.

The chip 14 is configured to be inserted into the portable control unit 16, shown in FIG. 6, for detection of microorganisms in the sample through an analysis of the sample's DNA. DNA analysis involves amplification of a portion of a specific pathogen's DNA and labeling the amplified DNA with a tag such a fluorescent tag. Specificity of amplification is achieved with the primers in the PCR reaction mix. Labeling of the amplified DNA may occur during the amplification process if DNA binding fluorescent dyes such as SYBR Green are included in the PCR reaction mix. Alternatively, the primers themselves may be labeled. Cyanine Dyes other than SYBR Green may be used as well as other classes of fluorescent dyes including acridine dyes, fluorone dyes, oxazine dyes, phenanthridine dyes, or Rhodamine dyes. In addition, other classes of labeling molecules may be used including colorometric, bioluminescent or chemiluminescent molecules, semiconductor quantum dots, and lanthide doped compounds or nanoparticles. As an example, fluorescence intensity from labeled amplified DNA can be continuously monitored during the PCR reaction. Fluorescence monitoring requires a light source 100 to excite the fluorophore, filters 104 or monochromators to reduce background from radiation of unwanted wavelengths, a lens 110, a detector 102 of the fluorescence that also converts the light signal to an electrical signal and a data acquisition card for digital readout. In addition, mirrors 106 may need to be incorporated to direct the path of light or alternatively, fiberoptic cables 108 may be used. The excitation energy may be supplied by lamps, light emitting diodes (LED) or lasers. Examples of lamps include tungsten halogen, quartz tungsten halogen, xenon arc and mercury vapor. After excitation, the fluorophore releases energy at a longer wavelength and this energy is detected by the photodetector. Photodetectors include charge coupled devices (CCD), photodiodes, photomultipliers, metal-semiconductor-metal (MSM), phototransistors, photoresistors, and pyroelectric photodetectors. Thus, as the pathogen specific DNA fragment is amplified, more fluorescent dye is bound and excited leading to more signal reaching the photodetector and data acquisition card. In the exemplary embodiment, software upgrades and pathogen specific information are downloadable to the microprocessor 76 to facilitate analysis of the most up to date pathogens and microorganisms.

The control unit 16 includes a digital display 78 that shows the results of the DNA analysis and a built-in battery unit/power supply 80 that allows mobility of the unit 16. In one embodiment, the control unit 16 further includes a global positioning satellite unit 82 to facilitate tracking detected plant pathogens and microorganisms globally and/or to facilitate real-time reporting of bioterrorism threats. The control unit 16 may also include file transfer software that transfers information from the microprocessor 76 to a centralized database 84, as shown in FIG. 1, where the global position of plant pathogens and bioterrorism threats are stored. In the exemplary embodiment, an input/output port 86 is provided to connect the control unit to a personal computer.

Accordingly, the present invention provides a portable microorganism detection device 10 that is capable of detecting microorganisms on food items, crops, seeds, or other biological materials at a point of use. Specifically, the device 10 is operable at the point of use and provides immediate analysis of contaminants such as pathogens and bioterrorism agents. The present invention further provides a device 10 capable of tracking and reporting pathogen and bioterrorism threats in real-time.

Figure 8:
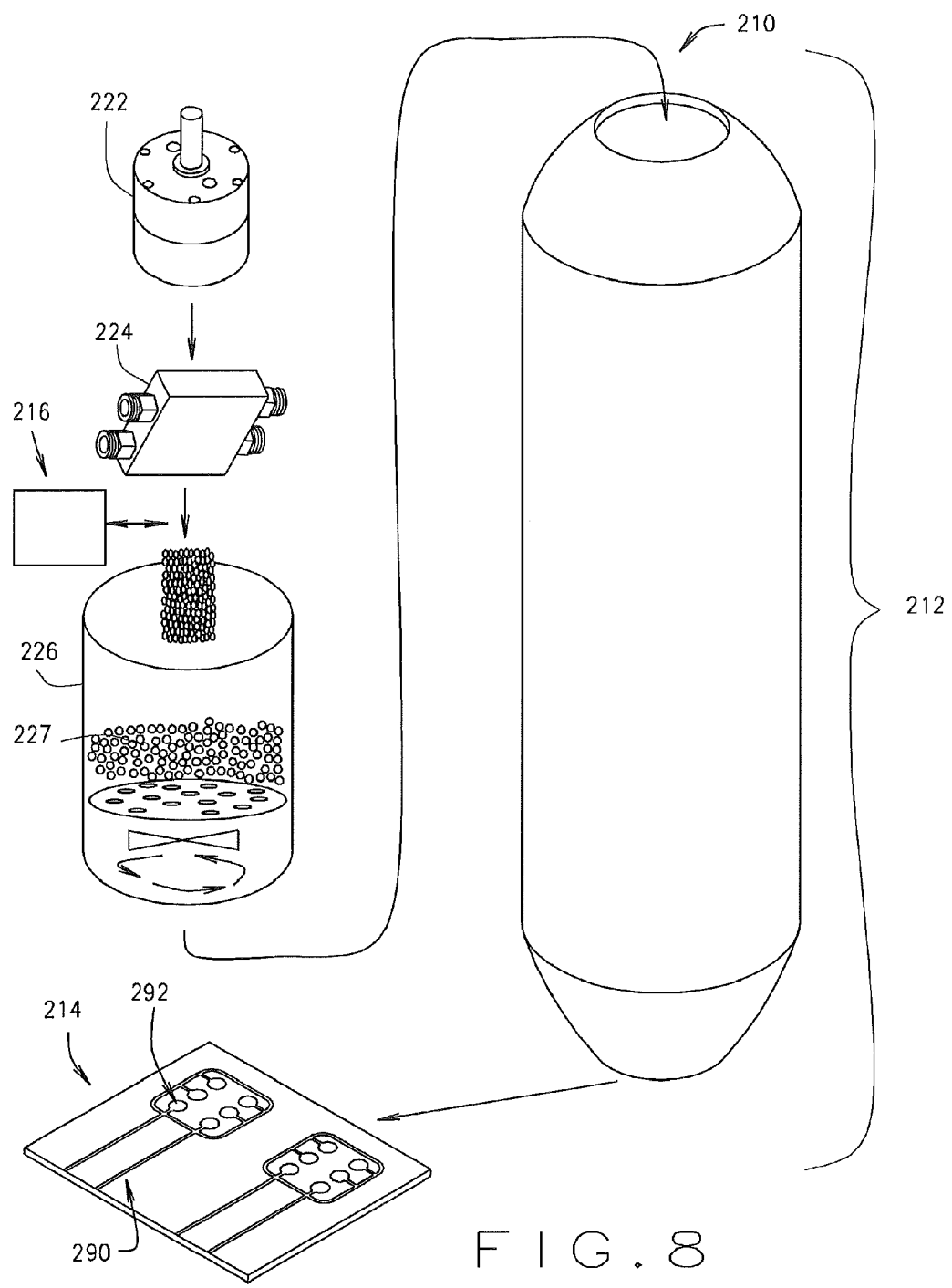
FIG. 8 is a block diagram showing components of a DNA extraction device in accordance with one embodiment of the present invention.

A portable apparatus 212 for extracting and purifying DNA from whole food or tissue samples or other biological materials (e.g. 25 g of meat, vegetable, seed, fruit, etc.) is illustrated in FIG. 8. This portable apparatus 212 may be configured as a stand-alone unit from which the purified DNA will be used in a desktop or handheld real-time PCR instrument for identification and quantification of contaminants such as food born pathogens. Alternatively, portable apparatus 212 may be integrated with analytical instrumentation and methods to give one device 210 that performs both sample preparation and DNA analysis by PCR. In this arrangement, the purified DNA from apparatus 212 can be delivered to the PCR Chip 214 in the control unit 216 of the device 210. Referring to the drawings more particularly by reference numbers, the numeral 212 in FIG. 8 identifies one embodiment of a DNA extraction device, more particularly a portable apparatus for extracting nucleic acid (i.e. DNA or RNA) from a biological sample constructed in accordance with the teachings of the present invention. The DNA extraction device 212 can be manufactured so as to be compatible for attachment to any suitable type of device for detecting pathogens and bioterrorism molecules in biological materials. For example, the device may be configured to detect pathogens such as soybean rust, wheat scab, corn ear rot, *Salmonella, Listeria, Escherichia coli*, and/or bioterrorism threats such as anthrax, bubonic plague, and/or yellow fever that are contained in food products such as meat, bottled water, fresh vegetables, dairy, seafood, and grains. In one embodiment, the DNA extraction device 212 is portable so that the detection can take place at a point-of-use or, for example, at the location where food is grown and/or produced. The DNA extraction device 212 can be configured as a stand-alone device or can be integrated into a device 210 for detecting contaminants such as plant and food pathogens and bioterrorism molecules.

As shown in FIG. 8, a portable device 210 for detecting microorganisms includes a DNA extraction device 212 for extracting and purifying a DNA eluate from the sample, a chip 214 configured to retain and react with the eluate to specifically amplify a portion of the DNA, and a portable control unit 216 configured to pressurize the DNA extraction device 212. The control unit 216 is also configured to receive the chip 214 and analyze the amplified DNA. Although the present invention is described with respect to detecting microorganisms on food products, as will be appreciated by one of ordinary skill in the art, the present invention may be used to detect microorganisms on a vast array of products or in a multitude of settings including medical/veterinary point-of-care and field environmental settings.

Figure 9:
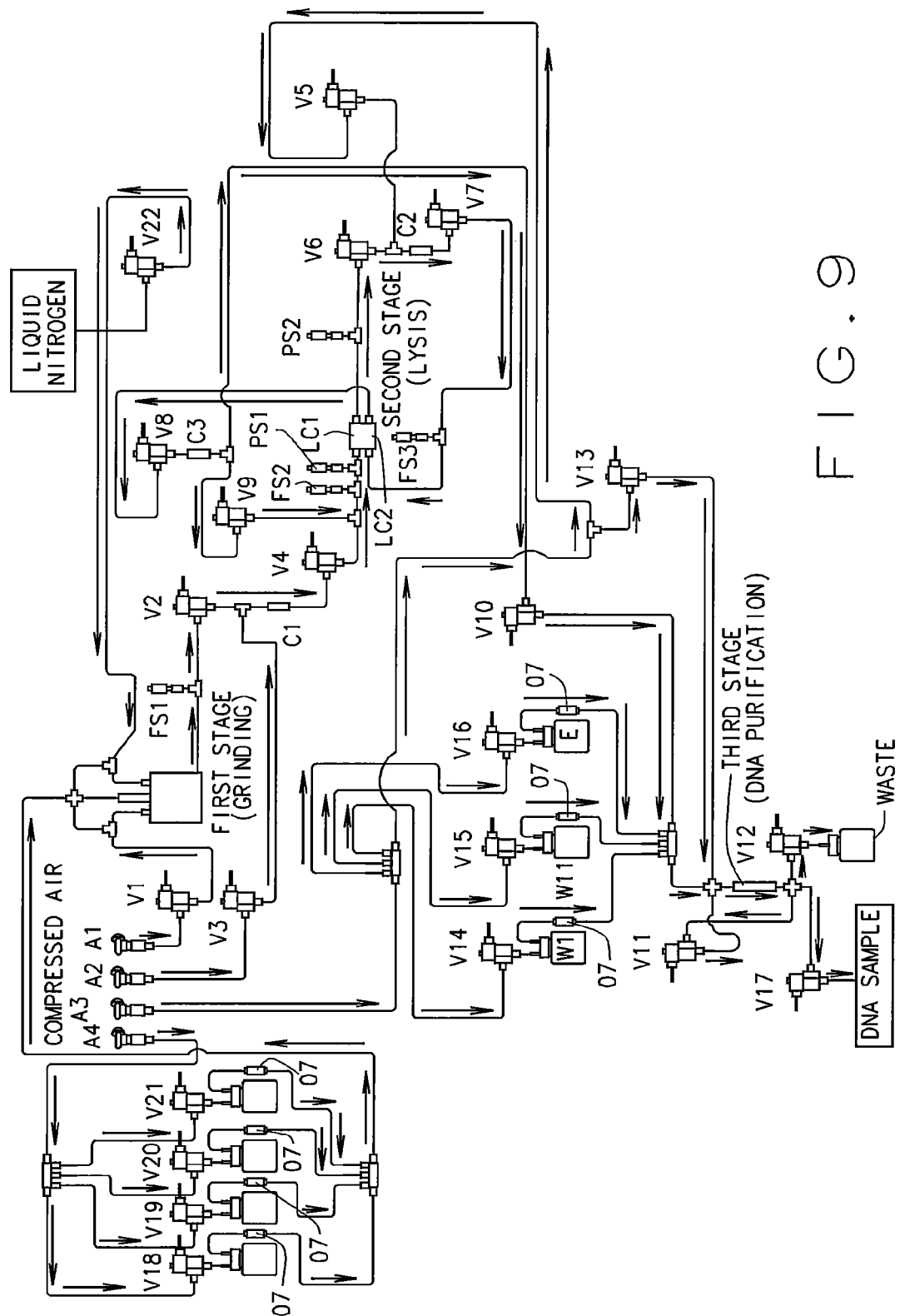
FIG. 9 is a combined schematic view and process flow diagram for a DNA extraction device, showing connections between each component of the DNA extraction device.

The DNA extraction device 212, of the present invention as shown in FIGS. 8 and 9, includes three chambers or segments separated by connecting fluid channels, specifically, a first segment 222, a second segment 224 and a third segment 226. The DNA extraction device 212 includes a first chamber or segment 222 for mechanically breaking down a frozen food sample, a second chamber or segment 224 for pressurizing the mixture of the processed food sample and lysis solution in order to produce a resulting lysate, and a third chamber or segment 226 for purifying DNA in the resulting lysate as illustrated in FIG. 8.

Figure 10:
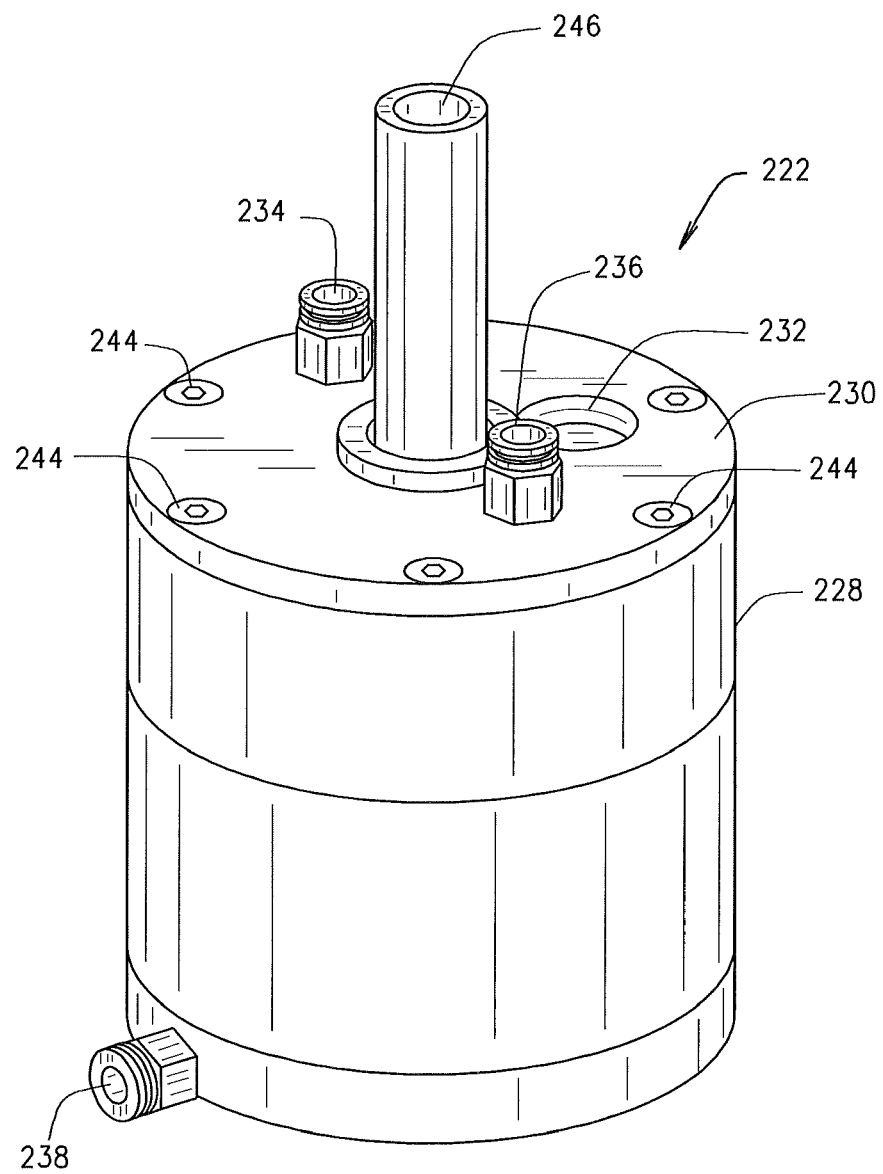
FIG. 10 is a perspective view of a grinding chamber used with the DNA extraction device in accordance with one embodiment of the present invention.
Figure 10B:
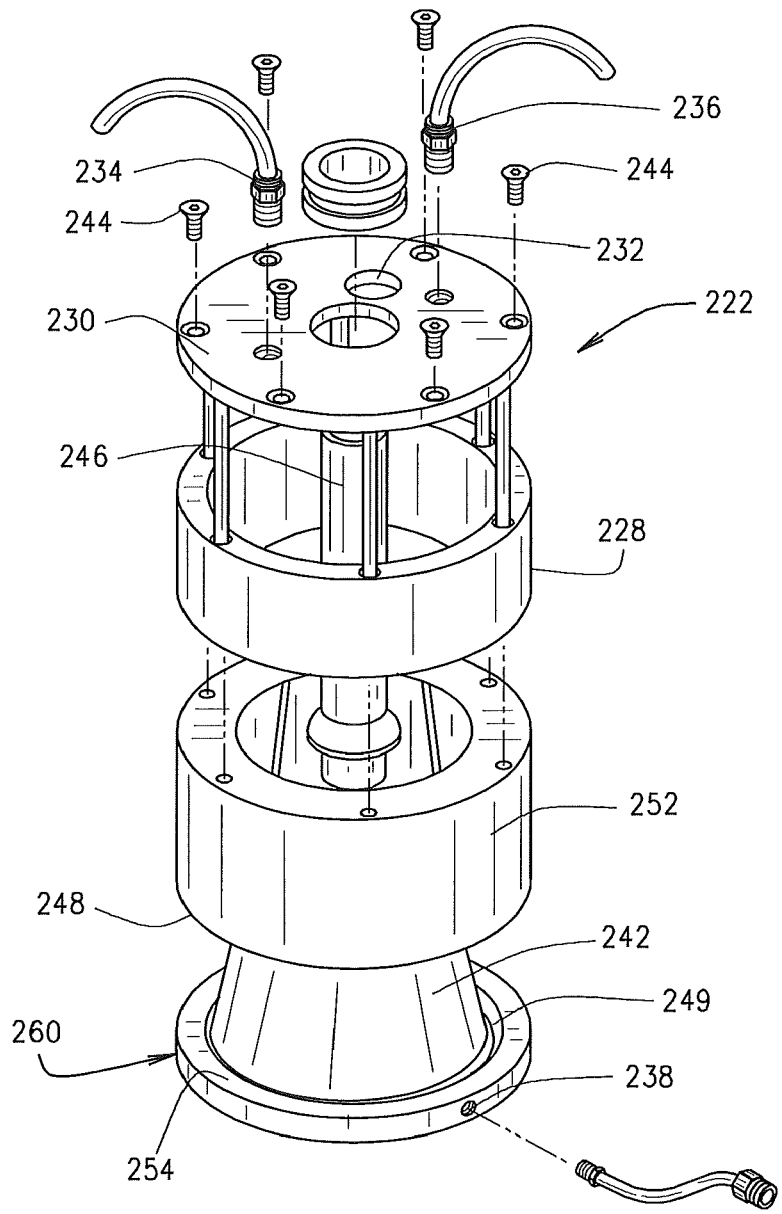
FIG. 10B is an exploded view of the grinding chamber shown in FIG. 10.

As an overview, as best seen in FIGS. 10, 10A and 10B, the process of the first segment generally comprises first freezing a food sample, and then disrupting the frozen food sample, particularly a solid sample, by mechanically breaking down the frozen sample, for example, by grinding, mincing, or pulverizing. The DNA extraction device 212 includes a generally hollow cylindrically shaped first chamber 222 for mechanically breaking down a frozen food or tissue sample.

In one embodiment of the apparatus 212, the first chamber 222 incorporates a grinding mechanism for grinding a sample and includes a cylindrical body 228, a top cover 230, three inlet openings 232, 234, 236, an outlet 238, an outer grinding member 240 and an inner grinding member 242 positioned within the outer grinding member 240. The top cover 230 is disposed at the top of the cylindrical body 228 and secured to the cylindrical body by multiple securing means 244, such as bolts, spaced apart along the peripheral edge of the round-shaped top cover 230. The top cover 230 forms a closable first inlet opening 232 of a desired shape for allowing a user to feed a food sample therethrough. A food sample is placed in the first chamber 222 through the first inlet opening 232. In the exemplary embodiment, the food sample is approximately 25 grams.

FIG. 9 represents a process flow diagram for a preferred embodiment of the present invention. A food sample is first added to the first chamber 222. Valve V22 is opened to allow liquid nitrogen to flow from a tank or other source to the first chamber 222 to freeze the sample within the first chamber 222.

The sample is then ground under the influence of a centrifugally responsive inner grinding member 242 acting against an outer grinding member 240. The inner grinding member 242 is rotatably mounted for grinding the frozen food sample. The crushing or grinding chamber 222 of the DNA extraction device 212 includes a motor (not shown) for rotating the inner grinding member 242. The grinding chamber or segment 222 further includes a drive shaft 246 which is rotatably coupled to the inner grinding member 242 within the appropriate structure associated with the inner grinding member 242 such as a centrally located sleeve (not shown). The sleeve will house appropriate connection means including a suitable grind head assembly for attaching the drive shaft 246 to the inner grinding member 242. The inner grinding member 242 is positioned offset from the center of the grinding chamber 222 such that the inner grinding member 242 oscillates in an asymmetric fashion and is supported by the drive shaft 246 during operation of the inner grinding member 242. The drive mechanism for the drive shaft 246 includes the driving motor (not shown). The drive shaft 246 extends from the driving motor through an opening disposed at the center of the top cover 230 to the inner grinding member.

An outer grinding member 240 is comprised of at least one cylindrical member 252, such as a sleeve or tube securely locked to an outer end of a mounting disk 254 to prevent rotation, preferably by the bottom peripheral edge 248 of the outer grinding member 240 are positioned to mate with a slot 249 formed on the mounting disk 254. The inner grinding member 242 forming a truncated-cone shaped external surface is positioned within the outer grinding member 240 to form a tapered annular gap 256 therebetween. The gap 256 is tapered from the top to the bottom of the inner grinding member 242. The inner grinding member 242 having an overall tapered profile is fastened to a base 260. Advantageously, the inner grinding member 242 comprises a truncated conical outer surface. Both the inner surface of the outer grinding member 240 and the outer surface of the inner grinding member 242 are engaged with the food sample. The frozen food sample is ground as it is banged against the inner surface of the outer grinding member 240 from the outer surface of the inner grinding member 242 oscillating in an asymmetric manner. When the drive shaft 246 is moved axially by the driving motor, the inner grinding member 242 is moved axially relative to outer grinding member 240 to adjust the gap size.

In a preferred embodiment, the grinding chamber 222 is comprised of hard material suitable for autoclaving, withstanding impact forces, and resistance to heating up and harsh chemicals—i.e. lysis solution (Guanidine hydrochloride, Guanidine thioisocyanate, Potassium iodide or Sodium iodide).

Although the specific apparatus disclosed and discussed herein is directed to a mechanism for grinding dry or frozen food sample, other types of mechanism for mechanically breaking down, i.e., processing, the dry or frozen biological sample can also be used in the present invention without departing from the spirit and scope of the invention. For example, the mincing mechanism described herein may be utilized. Alternately, the first chamber may comprise one or more cutting blades rotated at high rpm and through which the biological sample is forced.

In one embodiment, the motor is engaged to operate the inner grinding member 242 for 1-5 minutes at approximately 50 rpm.

Upon completion of grinding, valve V18, which is connected with a source of pressurized air A4, is opened to allow a lysis solution to flow from a tank or other source into the first chamber 222. Immediately thereafter, valve V1, which is connected with a source of pressurized air A1, and V2, which is connected with a first collection chamber C1, are opened to force the mixture of ground food and lysis solution from the first chamber 222 to the first collecting chamber C1. In one embodiment, pressurized air source A1 provides 30 to 40 psi. A flow sensor FS1 may be incorporated into the flow path between the first chamber 222 and the first collecting chamber C1. The flow sensor FS1 operates to close valves V1 and V2 once the flow of material from the first chamber 222 ceases, at which time all material from the first chamber 222 should have been transferred to the first collecting chamber C1. Alternately, valves V1 and V2 may simply be opened for a set period of time and then closed under the control of a programmable logic controller or other control device. In alternate embodiments, a pump may be incorporated into the device at its output end in order to introduce a partial vacuum within the device flow paths to accomplish the same movement of the sample through those flow paths. Those of skill in the art will recognize that the pressure used to motivate the sample through the device may be created through multiple methods.

The next step in the process involves transferring the ground sample/lysis solution combination from the first collecting chamber C1 to the second segment 224. To do so, valve V3, which is connected to pressurized air source A2, is opened to expose the contents of the first collecting chamber C1 to a motive pressure. Valve V4 is opened to allow the contents of the collecting chamber C1 to travel to the second segment 224. Valve V6 is opened to allow the sample to travel from the second segment 224 to a second collecting chamber C2. A second flow sensor FS2 may be incorporated into the flow path between the first collecting chamber C1 and the second segment 224. The flow sensor FS2 operates to close valves V3, V4, and V6 once the flow of material from the first collecting chamber C1 ceases, at which time all material from the first collecting chamber C1 should have been transferred through the second segment 224 and into the second collecting chamber C2. In alternate embodiments, valves V3, V4, and V6 may simply be opened for a set time period and then closed under the control of a programmable logic controller or other control device. If additional pressure is required or desired for this transfer of the food sample from the first collecting chamber C1, valves V1 and V2 may be opened as well. Pressure sensors PS1 and PS2 may be incorporated into the flow path at the inlet and outlet, respectively, of the second segment to monitor the pressure to which the sample is exposed during this transfer. In alternative embodiments, valves V1 and V2 may simply be opened for a set time period and then closed under the control of a programmable logic controller or other control device.

Figure 11A:
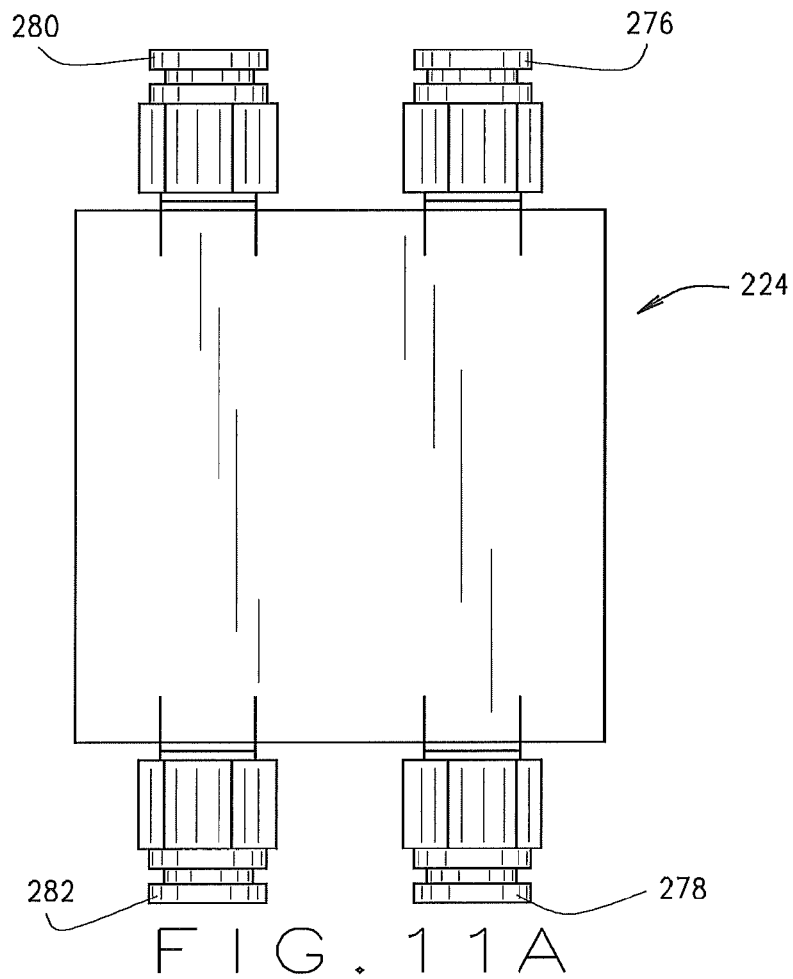
FIGS. 11A and 11B are views of a pressurizing chamber shown in FIG. 10 in accordance with one embodiment of the present invention.
Figure 11B:
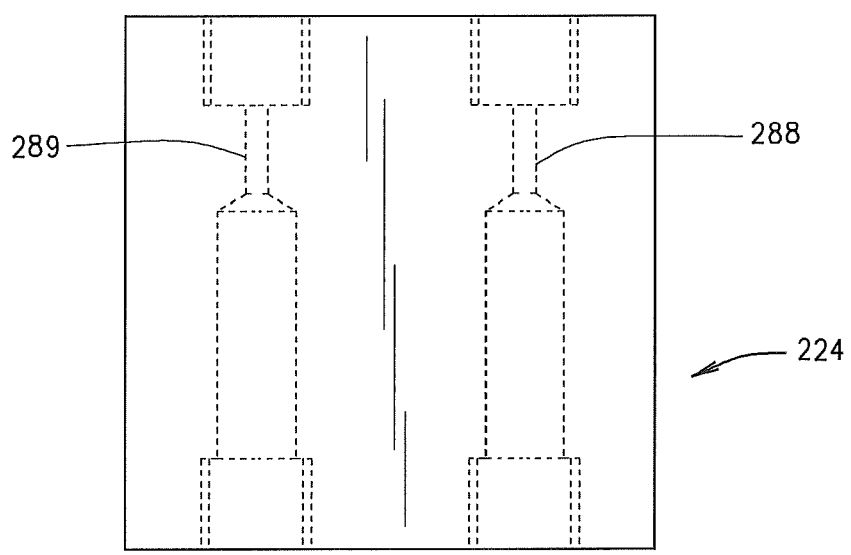

As best shown in FIGS. 9, 11A and 11B, the second chamber or segment 224 of the DNA extraction device 212 functions in inducing pressure fluctuations on the ground sample solution. The second chamber segment 224 of the DNA extraction device 212 includes two pairs of ports, a first inlet port 276, a first outlet port 278, a second inlet port 280, and a second outlet port 282, shown in the form of a circular opening. A first orifice or stricture 288 is positioned between the first inlet port 276 and the first outlet port 278 within the second segment 224. The combination of first inlet port 276, stricture 288, and first outlet port 278 is also referenced as a first lysis chamber LC1 on FIG. 9. A second orifice or stricture 289 is positioned between the second inlet port 280 and the second outlet port 282 within the second segment 224. The combination of second inlet port 280, stricture 289, and second outlet port 282 is also referenced as a second lysis chamber LC2 on FIG. 9. The food sample is circulated through the first LC1 and second LC2 lysis chambers in order to subject the sample to rapid pressure fluctuations. Lysis chambers LC1 and LC2 are orifice reduction chambers that facilitate movement of the food sample slurry from a relatively large diameter to a relatively smaller diameter and back to a larger diameter to achieve lysis, i.e. bursting of the cell walls, to release bacterial DNA from inside of the bacterial cell. The pressure fluctuation involved in one embodiment is on the order of 4500 to 5000 psi; however, the degree of pressure fluctuation may vary in different embodiments and applications and may involve higher or lower pressure levels. More particularly, movement of the slurry out of the lysis chambers results in a rapid drop in pressure on the liquid. Pressure of liquid drops faster than the intracellular pressure, resulting in cell explosion. In a preferred embodiment, the second segment 224 is able to withstand a minimum of 10,000 psi and is autoclavable.

While the second segment 224 illustrated in FIGS. 11A and 11B incorporates round orifices, other types of orifice design may be utilized and are considered to be within the scope of the present invention. Alternatives includes a rectangular design, or a rectangular or circular design having alternating "teeth" around the edge of the orifice. In the case of the last exemplary alternative, the teeth around the edge are provided to increase the surface area of the orifice edge to maximize the shear forces on the sample as it is passed through the orifice. This is accomplished due to the fact that a greater portion of the sample is placed into direct contact with the orifice edge during each pass.

The food sample is transferred from the second collecting chamber C2, through the second lysis chamber LC2, and into a third collecting chamber C3 by opening valve V5, which is connected to pressurized air source A3, to expose the contents of the first collecting chamber C2 to a motive pressure. Valve V7 is opened to allow the contents of the second collecting chamber C2 to travel back to the second segment 224 and pass through the second lysis chamber LC2. Valve V8 is opened to allow the sample to travel from the second segment 224 to a third collecting chamber C3. A third flow sensor FS3 may be incorporated into the flow path between the second collecting chamber C2 and the second segment 224. The flow sensor FS3 operates to close valves V5, V7, and V8 once the flow of material from the second collecting chamber C2 ceases, at which time all material from the second collecting chamber C2 should have been transferred through the second lysis chamber LC2 and into the third collecting chamber C3. In alternate embodiments, valves V5, V7, and V8 may simply be opened for a set time period and then closed under the control of a programmable logic controller or other control device. If additional pressure is required or desired for this transfer of the food sample from the second collecting chamber C2, valves V1, V2, V4, and V6 and/or V3, V4, and V6 may be opened as well.

In order to move the sample from the third collecting chamber C3 back through the first lysis chamber LC1, valves V5, V7, V8, V9, and V6 are opened to pressurize the line and force the sample from the third collecting chamber C3, through the first lysis chamber LC1 and back to the second collecting chamber C2. In the preferred embodiment, the food sample is cycled alternately through the lysis chambers LC1 and LC2 a total of ten (10) times. However, the number of cycles may vary.

Once the food sample slurry has been cycled through the lysis chambers LC1 and LC2 an appropriate number of times to result in the desired cell lysis, the slurry is transferred from the second segment 224 to the third segment 226 for DNA purification. In some embodiments, the slurry is passed through a filter, not shown, located between the second segment 224 and the third segment 226 to clarify the lysate and remove particulates. However, the filter is optional. In the illustrated embodiment, this transfer is made by opening valves V5, V7, V8, V10, and V11 to pressurize the flow path and allow the slurry to flow to the third segment 226 and cycle repeatedly therethrough.

In one embodiment, the third segment 226 is a DNA purification column. The column includes a binding material that binds to the DNA present in the solution. In the exemplary embodiment, the binding material includes silicon dioxide resin that binds to the DNA present in the sample. Other DNA binding reagents may be employed including silica beads, silica gel, silica membrane, glass fiber, diatomaceous earth, ion-exchange resin, iron oxide particles or ligand exchange resins. DNA molecules bind to silica, glass, and diatomaceous earth in the presence of high salt concentrations (e.g. Sodium Iodide or Guanidinium Hydrochloride) and low pH.

After washing in an ethanol containing high salt buffer, the DNA can be eluted from the silica, glass or diatomaceous earth in a high pH (e.g. pH=8 to 8.5) buffer with low salt concentrations. Ion exchange resins and iron-oxide take advantage of charge-charge interactions for binding DNA. For example, diethylaminoethanol (DEAE) has a positive charge under low salt and low pH conditions and will bind to the negative charge on the DNA phosphate backbone. DNA can be eluted from DEAE under high salt and high pH conditions. The resin or support for ion exchangers can consist of silica, cellulose, dextran or agarose. Iron oxide has the added advantage of magnetism to facilitate collection and concentration of the DNA bound iron-oxide particles.

The silicon dioxide resin is a fifty percent (50%) mixture of silicon dioxide and water. During the five (5) minute incubation of the clarified lysate with the silica resin, DNA binds to the silica. After DNA binding, silica resin is washed two times with 10 mL to 20 mL of wash solution each time. Each wash is for five (5) minutes with continual mixing. The washes remove proteins, carbohydrates, and other unwanted cellular contents. After these two washes, DNA is collected off the silicon dioxide resin using 1 mL to 2 mL of an elution solution. Ideally, the elution solution is hot to begin with (50° C. to 60° C.) and mixed (continual mixing) with the silica for five (5) minutes. Elution solution is collected for analysis on an analytical device.

More specifically, during extraction of the DNA, the DNA in the solution binds to the silica beads forming a bead slurry. The bead slurry is then mixed by fluid flow or vibration for an incubation period of approximately five minutes. After the incubation period, the solution is drained through the waste port 266 leaving the silica beads having DNA bound thereto. The beads are then washed with the wash solution. For example, the beads 227 may undergo two washes for approximately five minutes each. The wash solution is then drained off and the hot elution buffer having a temperature of approximately 60 degrees Celsius is added to the third chamber and mixed with the silica beads for approximately five minutes to form the eluate. The eluate is drained through the elution outlet to the chip 214. In the exemplary embodiment, at least one of circuitry, micropumps, microvalves, and/or microheaters/coolers are used to move the eluate from the DNA extraction device 212 to the chip 214 and/or to maintain a uniform temperature of the eluate when moving the eluate.

As will be appreciated by one of ordinary skill in the art, other types of purifying mechanism for the DNA extracted from food sample can also be used in the present invention without departing from the spirit and scope of the invention.

In the illustrated embodiment, the above process is shown with two separate wash solutions WI and WII and one elution solution E. Flow of the wash solutions WI and WII and elution solution E is controlled by valves V14, V15, and V16, respectively, which are each connected with pressurized air source A3. More particularly, valve V14 is first opened to allow wash solution WI to flow from a source to the purification column. Valves V13 and V11 are opened to cycle the wash solution WI through the purification column for a set period of time and/or cycles. Valve V12 is then opened to allow the wash solution WI to pass to a waste container.

Next, valve V15 is opened to allow wash solution WII to flow from a source to the purification column. Again, valves V13 and V11 are opened to cycle the wash solution WII through the purification column for a set period of time and/or cycles. Valve V12 is then, once again, opened to allow the wash solution WII to pass to a waste container.

Finally, valve V16 is opened to allow the elution solution E to flow from a source to the purification column. Again, valves V13 and V11 are opened to cycle the elution solution E through the purification column for a set period of time and/or cycles. However, this time valve V17 is opened to allow the purified DNA sample to pass to a collection tube or an analytical device for evaluation. As shown in FIG. 8, the chip 214 includes a plurality of microchannels 290 in fluid communication with a plurality of reaction chambers 292 etched within the chip 14. The eluate is channeled via the microchannels 290 to the reaction chambers 292 where a polymerase chain reaction takes place (PCR) to amplify the DNA in the eluate for detection. Specifically, the reaction chambers 292 include reagents, for example lyophilized nucleotides, DNA polymerase, pathogen specific primers, fluorescent labeling molecules such as SYBR green, and/or reagents specific to a type of PCR that are disposed to create a PCR reaction that specifically amplifies a portion of the DNA on the chip 214. It will be appreciated by one of ordinary skill in the art that the number, size, and orientation of the microchannels 290 and reaction chambers 292 may vary depending on the application of the chip 214. Specifically, the chip 214 is configured to be customized for the detection of various microorganisms. The number, size, and orientation of the microchannels 290 and the reaction chambers 292 may vary based on the particular microorganism sought to be detected. Moreover, in one embodiment, the chip 214 may be configured to detect multiple microorganisms through a single analysis. For example, the meat processing industry is concerned mainly with *Escherichia coli, Listeria monocytogenes* and *Salmonella* species. Customized cards for detecting these pathogens could be developed. Processors of fresh fruits and vegetables focus on bacteria such as *E. coli, Salmonella, Vibrio cholera,* and *Shigella;* protozoa such as *Cryptosporidium parvum, Toxoplasma gondii, Giardia lamblia, Cyclospora cayetanensis;* and viruses such as Norwalk and Hepatitis A. For this food processor, custom bacterial, protozoan and viral cards or various combinations could be developed. The dairy industry is concerned with bacterial species from the following genera: *Psuedomonas, Bacillus, Clostridium, Corynebacterium, Arthrobacter, Lactobacillus, Microbacterium, Micrococcus, Streptococcus, Listeria, Escherichia, Yersenia, Salmonella,* and *Campylobacter.*

The chip 214 is configured to be inserted into the portable control unit, not shown, for detection of microorganisms in the sample through an analysis of the sample's DNA. DNA analysis involves amplification of a portion of a specific pathogen's DNA and labeling the amplified DNA with a tag such as a fluorescent molecule. Specificity of amplification is achieved with the primers in the PCR reaction mix. Labeling of the amplified DNA may occur during the amplification process if DNA binding fluorescent dyes such as SYBR Green are included in the PCR reaction mix. Alternatively, the primers themselves may be labeled. Cyanine Dyes other than SYBR Green may be used as well as other classes of fluorescent dyes including acridine dyes, flurone dyes, oxazine dyes, phenanthridine dyes, or Rhodamine dyes. In addition, other classes of labeling molecules may be used including colorometric, bioluminescent or chemiluminescent molecules, semiconductor quantum dots, and lanthide doped compounds or nanoparticles. As an example, fluorescence intensity from labeled amplified DNA can be continuously monitored during the PCR reaction.

It is noted that alternate embodiments may involve transmission of the purified DNA sample to a vial or other sample collecting means for transfer to a separate analytical device.

The control unit 216 includes a digital display that shows the results of the DNA analysis and a built-in battery unit/power supply (not shown) that allows mobility of the unit 210. In the exemplary embodiment, an input/output port (not shown) is provided to connect the control unit to a personal computer. The control unit 216 further includes a microprocessor, and may also include a battery and/or a GPS component.

Accordingly, the present invention provides a portable microorganism detection device 210 that is capable of detecting microorganisms on food items, crops, or seeds at a point of use of the food item, crop or seed. Specifically, the device 210 is operable at the crop site/production site and provides immediate analysis of pathogens and bioterrorism agents. The present invention further provides a device 210 capable of tracking and reporting pathogen and bioterrorism threats in real-time.

Those of skill in the art will recognize that an important aspect of the disclosed device is the ability to effectively cleanse the device after use in preparation for a new sample. In reference to the embodiment of FIG. 9, the following steps may be utilized for cleaning the device. First, a solution of up to 10% bleach is provided and connected through a valve V19 to the first segment 222. Valve V19 is opened to allow the bleach solution to flow into the first segment. The bleach solution is then forced from the first segment, through the lysis chambers, and through the purification column in the same manner as a sample is transferred as outlined above. Once the bleach solution has been cycled through the system for the desired amount of time, valve V12 is opened to dispose of the bleach solution.

In a preferred embodiment, this cycle is then repeated: first with pure water (controlled by valve V20) and finally with a seventy percent (70%) alcohol solution (controlled by valve V21). A final blow of air through the system serves as a drying process.

In the illustrated embodiment, the lysis solution, bleach solution, water, and alcohol solutions are all connected to a pressurized air source A4. Further, one-way valves 07 are utilized in connection with each of these sources to prevent backflow of solution. Similarly, one-way valves may also be connected to the wash solutions and elution solution sources.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow. The scope of the disclosure is not intended to be limited to the embodiments shown herein, but is to be accorded the full scope consistent with the claims, wherein reference to an element in the singular is not intended to mean "one and only one" unless specifically so stated, but rather "one or more."

What is claimed is:

1. An apparatus for extracting DNA from a biological sample, the apparatus comprising:
    a first segment for grinding a frozen biological sample to produce a ground sample, the first segment comprising:
    a base;
    an outer grinding member defining a cylindrical hollow structure, said outer grinding member attached to a top surface of said base;
    a rotatable inner grinding member being gradually tapered upwardly, the inner grinding member being positioned within said outer grinding member to form a tapered annular gap therebetween; and
    a lysis solution inlet configured to feed a predetermined quantity of lysis solution into the first segment; and
    a second segment for pressurizing a mixture of said ground sample and said lysis solution in order to produce a resulting lysate,
    wherein said first segment is fluidly coupled to said second segment.

2. The apparatus of claim 1, wherein said inner grinding member is positioned offset from a center of said base such that said inner grinding member oscillates in an asymmetric manner.

3. The apparatus of claim 1, wherein said second segment includes at least one stricture and said mixture of said ground sample and said lysis solution passes through said stricture.

4. The apparatus of claim 1, wherein said second segment includes a plurality of strictures and said mixture of said ground sample and said lysis solution passes through each of said strictures.

5. The apparatus of claim 1, further comprising a third segment comprising:
    means for exposing said resulting lysate to a binding material configured to bind to DNA of said sample; and
    means for collecting said DNA using an elution solution for analysis.

6. The apparatus of claim 1, further comprising a first fluid receiver positioned between said first segment and said second segment, wherein said first fluid receiver is in fluid communication with said first and second segments.

7. The apparatus of claim 1, further comprising a second fluid receiver and a third fluid receiver, wherein said second and third fluid receivers are in fluid communication with said second segment.

* * * * *